United States Patent [19]

Finney

[11] 4,204,530
[45] May 27, 1980

[54] SLEEVE IMPLANT
[75] Inventor: Roy P. Finney, Tampa, Fla.
[73] Assignee: Medical Engineering Corp., Racine, Wis.
[21] Appl. No.: 25,016
[22] Filed: Mar. 29, 1979
[51] Int. Cl.$^2$ ............................................... A61F 5/00
[52] U.S. Cl. ........................................................ 128/79
[58] Field of Search .................................. 128/79; 3/1
[56] References Cited

U.S. PATENT DOCUMENTS

| | | | |
|---|---|---|---|
| 1,206,324 | 11/1916 | Hart | 128/79 |
| 1,216,099 | 2/1917 | Falck | 128/79 |
| 2,868,192 | 1/1959 | Dannen | 128/79 |
| 2,899,957 | 8/1959 | Briggs | 128/79 |
| 3,939,827 | 2/1976 | Brunstetler | 128/79 |
| 4,009,711 | 3/1977 | Uson | 128/79 |

FOREIGN PATENT DOCUMENTS 554178  7/1932  Fed. Rep. of Germany ............. 128/79

*Primary Examiner*—Lawrence W. Trapp

[57] ABSTRACT

An implantable sleeve for increasing the penile diameter includes a flexible sheet of soft, physiologically acceptable implantable material, said sheet being of sufficient length when formed in the general shape of a cylindrical sleeve to extend from the glans penis to the base of the penis and of a width which is insufficient to completely encircle the penis, but sufficient to cover the corpora cavernosa. The sheet preferably has edges which are rounded and tapered side edges. The sleeve also includes suturing strips on the inside wall of the sleeve adjacent the side edges of the sheet which facilitate the suturing of the sheet to the tunica albuginea. The sleeve further includes porous patches located on the interior of the inside wall of the sleeve into which fibroblasts from the underlying tissues can grow to further anchor the sleeve to the tunica albuginea. In the preferred embodiment, the sheet is of very soft, medical grade silicone elastomer, and suturing strips are of Dacron fabric and the porous patches are of Dacron fabric or fluff.

10 Claims, 5 Drawing Figures

SLEEVE IMPLANT

The invention relates generally to surgically implantable devices, and more particularly, to penile implants.

BACKGROUND OF THE INVENTION

Impotence is defined as the inability of the male to achieve an erection of the penis of sufficient rigidity to permit sexual intercourse. Impotence is a common complaint in older males and may be caused by a variety of diseases and medications. Diabetes mellitus, spinal cord injury, peripheral vascular disease, and a number of drugs can cause sexual impotence.

Penile implants consisting of various shaped rods, commonly made of silicone elastomer, are implanted inside the corpora cavernosa to restore potency. While these devices do allow sexual intercourse, they do not always increase the penile diameter to an adequate size. After a penile implant, many men notice that their penis is significantly smaller than it was when they were able to achieve a normal erection.

SUMMARY OF THE INVENTION

It is the primary object of the present invention to disclose an implantable sleeve which increases the penile diameter.

The implantable sleeve of the present invention includes a flexible sheet of soft silicone elastomer or other appropriate material which may be implanted inside the human body with minimal reaction. The sheet is of sufficient length when formed in the general shape of a cylindrical sleeve to extend from the glans penis to the base of the penis and of a width that is insufficient to completely encircle the penis but sufficient to cover the corpora cavernosa. The sheet has fore and aft edges which are preferably rounded and tapered side edges. Suturing strips are attached to the inside wall of the sleeve adjacent to the side edges of the sheet to facilitate suturing the sleeve to the tunica albuginea. The sleeve further includes porous patches also located in the inside wall of the sleeve into which fibroblasts from the underlying tissues can grow to further anchor the sleeve to the tunica albuginea.

The implantable sleeve of the present invention is implanted between the penile skin and the tunica albuginea of the corpra cavernosa and anchored in place with sutures. The implantation may be performed separately as an augmentation procedure or in connection with the implantation of a penile implant to restore potency.

The implantable sleeve of the present invention increases the diameter of the penis while retaining sufficient softness. As a result, it improves the cosmetic appearance of the penis and also the functional use of the penis during intercourse.

DESCRIPTION OF THE PREFERRED EMBODIMENT

Figure 1:
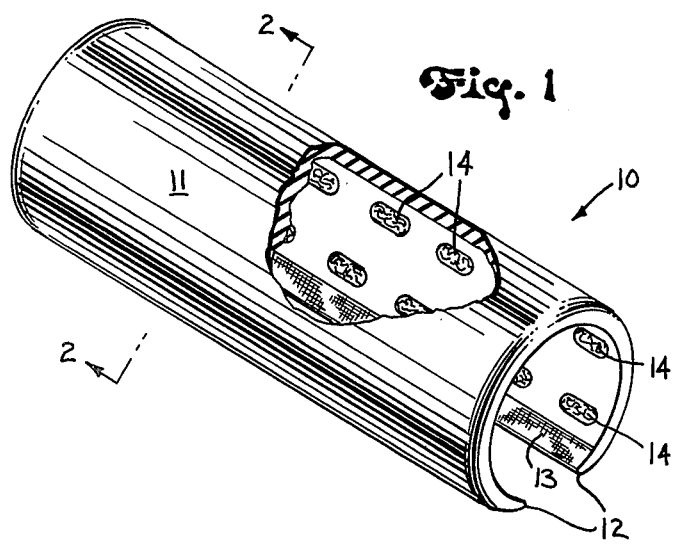
FIG. 1 is a perspective view of a preferred embodiment of the sleeve of the present invention.
Figure 2:
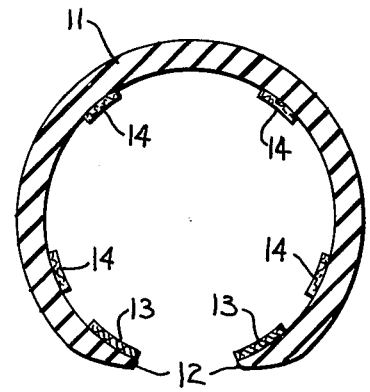
FIG. 2 is a sectional view taken along lines 2—2 of FIG. 1.

In the drawings, the implantable sleeve is generally identified by the numeral 10. As seen in FIGS. 1 and 2, the main body 11 of the sleeve 10 is in the shape of a partial cylinder having a crescent shaped cross section because of the tapered side edges 12.

The main body 11 of the sleeve 10 may be formed from a flexible, very soft sheet of a physiologically inert material such as medical grade, silicone rubber which has a length greater than its width. The softness of the rubber may be controlled by the type and amount of curing agent used to cure the elastomer and the amount of heat and time employed during the curing or vulcanizing process.

While the term "soft" is used in this specification and in the claims, as a convenient and generally understood description of the desired physical properties of the sheet, a more precise, technical term is flexural modulus; that is, the ratio of applied force to resulting deflection.

Softness may be measured by a durometer, such as a Shore A durometer which ascertains the depth of penetration of a specified indentor into a specimen under specified conditions. A scale is chosen so that "0" represents a material showing no measurable resistance to indentation and "100" represents a material showing no measurable indentation.

The softness of the rubber forming the main body 11 of the sleeve 10 will preferably have a Shore A softness of about 5 to about 20.

Referring to FIGS. 1 and 2 of the drawings, it can be seen that adjacent the tapered side edges 12 suturing strips 13 are attached to the inner wall of the main body 11 which facilitate the suturing of the sleeve 10 to penile tissue. The strips 13 are preferably strips of Dacron fabric and are glued to the inner wall of the body 11. Patches 14 of a porous or fibrous material such as sponge, fabric or fluff also are attached to the inner wall of the body 11 intermediate the tapered side edges 12. The patches 14 may also be of Dacron and provide pores, voids or fibrous areas into which fibroblasts from the underlying tissues can invade or grow to further anchor the sleeve in place when implanted.

Figure 3:
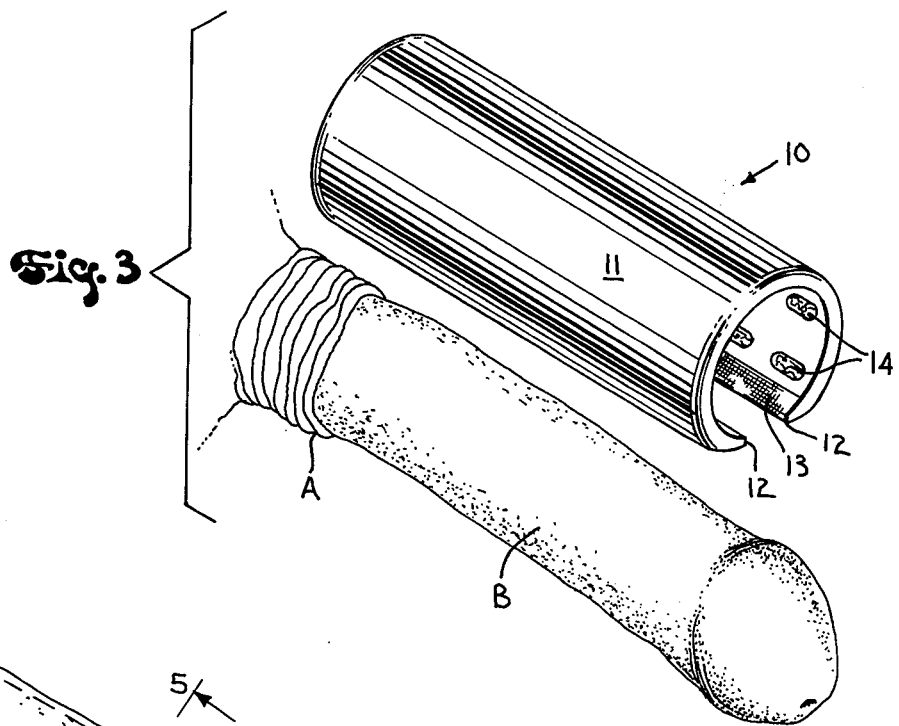
FIGS. 3 and 4 are perspective views showing the embodiment of FIG. 1 and the method of implantation.
Figure 4:
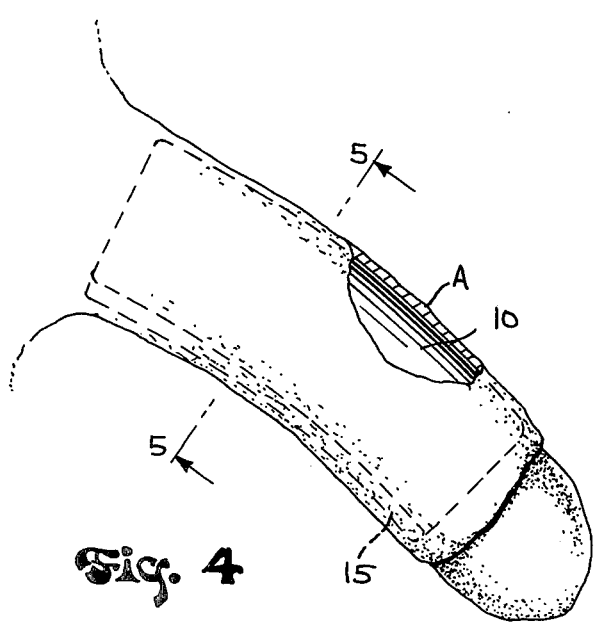

The method of implanting the sleeve 10 will be described in connection with FIGS. 3, 4 and 5.

The sleeve 10 is surgically implanted by first making an incision completely around the penile skin near the glans. The patient might be circumcized at this time if he had not had this done previously. The underside of the penile skin (A) is then dissected free of the underlying Buck's fascia and tunica albuginea (B). This area is relatively avascular and the dissection is easily accomplished. The skin is then retracted to the penile base as seen in FIG. 3 and the sleeve 10 is placed over the dorsum of the corpora cavernosa. A sleeve of the proper dimensions is selected so that the tapered edges 12 do not cover the corpus spongeosum of the urethra. The proper length of the sleeve 10 to extend from the glans penis to the base of the penis may be obtained by trimming the length of the sleeve 10 with scissors or a scalpel. The side edges 12 of the sleeve 10 are then sutured through the suturing strips 13 to the underlying Buck's fascia or tunica albuginea or both with sutures on both sides. The penile skin is then drawn over this sleeve 10 and reattached to the mucosal edge preferably with a two layer closure 15 as seen in FIG. 4.

Figure 5:
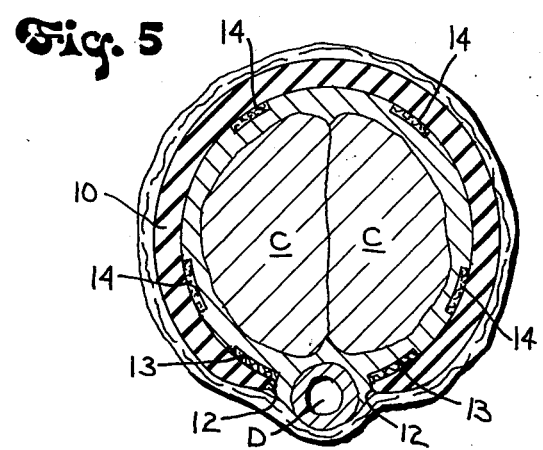
FIG. 5 is a cross sectional view taken along lines 5—5 in FIG. 4.

The correct position of the implantable sleeve 10 when in place is seen in FIG. 5. As seen therein the sleeve 10 does not completely encircle the penis which might result in obstruction of the urethra (D), but it only covers the corpora cavernosa (C).

The sheet forming the main body 11 of the sleeve 10 is about 2.5 mm thick and preferably has rounded end edges and tapered side edges. The sheet is preferably of silicone elastomer having the desired durometer and is about 80 to 100 mm long and about 100 mm wide. The Dacron fabric suturing strips 13 are preferably about 5.0 mm wide and run the entire length of the sheet adjacent the side edges. They are attached to what is to become the inner wall of the sleeve 10 with a suitable silicone adhesive. The preferred porous patches 14 are 2-3 mm × 7 mm pieces of Dacron fluff and are also attached to the inner wall with adhesive.

It will be readily apparent to those skilled in the art that a number of modifications and changes may be made without departing from the spirit of my invention. For example, in place of the continuous suturing strips 13 it may be possible to use patches or material for suturing and in place of porous patches, it may be possible to use continuous strips. Furthermore, the strips need not be fabric and the patches need not be porous in the strict sense of the word. Therefore, it is intended that the terms "strips," "patches," "fabric," and "porous" as used herein be broadly interpreted to cover obvious substitutions which perform the same functions.

In addition, it will be appreciated that although for purposes of illustration a sleeve having a main body formed of a sheet of rubber has been described, the main body could be a flat, envelope filled with a soft gel or of any other suitable functionally equivalent structure. Therefore, as used herein, the definition of the word "sheet" is intended to cover such functional equivalents.

In view of the foregoing, it will be understood that the invention is not intended to be limited except by the claims which follow.

I claim:

1. An implantable sleeve for increasing the diameter of a penis includes:
   (a) a soft, flexible sheet which can be formed into the shape of an elongated partial cylinder having a crescent-like cross section, said sheet having side edges which are tapered;
   (b) suturing strips attached to the wall of the sleeve that forms the inner wall of the cylinder, said suturing strips being located adjacent the tapered side edges of the sheet; and
   (c) porous patches located on the same wall of the sheet as the strips, said patches being located on the area of the wall intermediate the side edges.

2. The implantable sleeve of claim 1 in which the sheet is formed of a physiologically acceptable implantable material having a Shore A durometer of about 5 to about 20.

3. An implantable sleeve of claim 1 in which the sheet has a length of about 80 to about 100 mm and a width which is sufficient to cover the corpora cavernosa of a penis without covering the urethera.

4. The implantable sleeve of claim 1 in which the sheet is made of silicone elastomer.

5. The implantable sleeve of claim 1 in which the porous patches are of Dacron fabric or fluff.

6. An implantable sleeve of claim 1 in which the porous patches are of Dacron fabric or fluff.

7. An implantable sleeve for increasing the diameter of a penis which includes:
   (a) a flexible, soft sheet which when implanted assumes the shape of a partial cylinder having a crescentlike cross section, said sheet having end edges and tapered side edges, and a length sufficient to extend from the glans penis to the base of the penis and a width sufficient to cover the copora cavernosa but not the urethra of the penis;
   (b) suturing strips attached to a wall of said sheet adjacent the side edges to facilitate the suturing of the sleeve to the tissue of the penis to anchor the sleeve in place; and
   (c) patches attached to the same wall of the sheet as the suturing strips, said patches being positioned intermediate the tapered side edges and providing areas into which fibroblasts of the underlying tissue of the penis can grow to further anchor the sleeve in place.

8. The implantable sleeve of claim 7 in which the sheet is formed of a physiologically acceptable and implantable material having a Shore A durometer of about 5 to about 20.

9. The implantable sleeve of claim 7 in which the physiologically acceptable implantable material is silicone rubber.

10. The implantable sleeve of claim 7 in which the suturing strips and patches are of Dacron.

* * * * *